United States Patent
Thormann

(10) Patent No.: US 7,662,833 B2
(45) Date of Patent: Feb. 16, 2010

(54) IMIDAZO [1,2-A] PYRIDINE DERIVATIVES USEFUL AS PEPTIDE DEFORMYLASE (PDF) INHIBITORS

(75) Inventor: Michael Thormann, Martinsried (DE)

(73) Assignee: Novartis AG, Basel (CH)

( * ) Notice: Subject to any disclaimer, the term of this patent is extended or adjusted under 35 U.S.C. 154(b) by 95 days.

(21) Appl. No.: 11/912,325

(22) PCT Filed: Apr. 24, 2006

(86) PCT No.: PCT/EP2006/003767

§ 371 (c)(1),
(2), (4) Date: Oct. 23, 2007

(87) PCT Pub. No.: WO2006/114263

PCT Pub. Date: Nov. 2, 2006

(65) Prior Publication Data

US 2008/0188515 A1    Aug. 7, 2008

(30) Foreign Application Priority Data

Apr. 25, 2005  (DE)  .................. 10 2005 019 181

(51) Int. Cl.
*A01N 43/42*   (2006.01)
*A61K 31/44*   (2006.01)
*C07D 471/02*  (2006.01)
*C07D 491/02*  (2006.01)
*C07D 498/02*  (2006.01)

(52) U.S. Cl. ..................... 514/303; 546/118
(58) Field of Classification Search ............... 546/118; 514/303
See application file for complete search history.

(56) References Cited

U.S. PATENT DOCUMENTS

2004/0127719 A1 * 7/2004 Yang et al. .................. 548/406

FOREIGN PATENT DOCUMENTS

| EP | 0 632 040 A1 | 1/1995 |
| WO | WO 01/85170 A1 | 11/2001 |
| WO | 0230428 * | 4/2002 |
| WO | WO 03-101442 A1 | 12/2003 |
| WO | WO 2004/052919 A2 | 6/2004 |

OTHER PUBLICATIONS

Kiselyov et al., Tetrahedron Letters (2005), 46(26), 4487-4490.*
Ireland et al., Tetrahedron Letters (2003), 44(23), 4369-4371.*
Chen et al., Synlett (2001), (8), 1263-1265.*
Chen, Jack J. et al., "Multi-Component Synthesis of Imidazo[1,2-a] Annulated Heterocycles on .alpha.-Isocyano Resin Esters", Synlett, (8)1263-1265(2001). Thieme Stuttgart, New York, NY, US.

* cited by examiner

*Primary Examiner*—D. Margaret Seaman
*Assistant Examiner*—Niloofar Rahmani
(74) *Attorney, Agent, or Firm*—John Alexander

(57) ABSTRACT

The present invention relates to compounds of formula (I). These compounds are a novel type of peptide deformylase (PDF) inhibitors, and are therefore of great interest especially as new antibiotics.

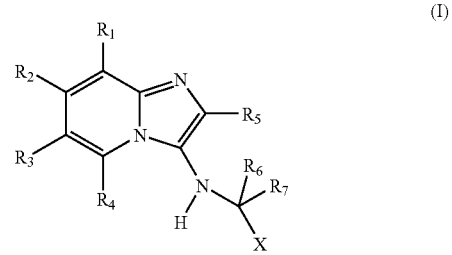

20 Claims, No Drawings

IMIDAZO [1,2-A] PYRIDINE DERIVATIVES USEFUL AS PEPTIDE DEFORMYLASE (PDF) INHIBITORS

This application is the National Stage of Application No. PCT/EP2006/003767 filed on Apr. 25, 2005, The contents are incorporated herein by reference in their entirety.

The present invention relates to new inhibitors of peptide deformylase (PDF). These compounds are of great interest in particular as antibiotics.

Peptide deformylase is a bacterial metalloenzyme which contains iron. It is detectable in all bacteria and plays a vital role in bacterial metabolism. During protein synthesis, peptide deformylase catalyses the removal of the formyl group from the N-terminus of bacterial proteins. Without the enzyme, bacteria cannot produce any functioning proteins. Peptide deformylase is the point of application of a new class of antibiotics, which are called peptide deformylase inhibitors.

It is the aim of the present invention to prepare new inhibitors of peptide deformylase that are obtainable synthetically in a simple manner.

The present invention relates to compounds of formula (I),

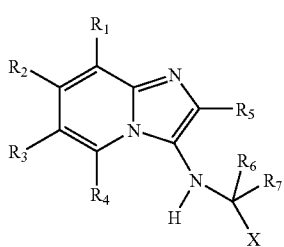

(I)

wherein the radicals $R^1$, $R^2$, $R^3$ and $R^4$, independently of one another, are a hydrogen atom, a halogen atom, a hydroxy, amino, nitro or thiole group, an alkyl, alkenyl, alkinyl, heteroalkyl, aryl, heteroaryl, cycloalkyl, alkylcycloalkyl, heteroalkylcycloalkyl, heterocycloalkyl, aralkyl or a heteroaralkyl radical, whereby all of these radicals may optionally be substituted, or two of the radicals $R^1$, $R^2$, $R^3$ and $R^4$ together may be part of a cycloalkyl, heterocycloalkyl, aryl or heteroaryl ring, whereby each of these rings may optionally be substituted;

$R^5$ is a hydrogen atom, a halogen atom, a hydroxy, amino, nitro or thiole group, an alkyl, alkenyl, alkinyl, heteroalkyl, aryl, heteroaryl, cycloalkyl, alkylcycloalkyl, heteroalkylcycloalkyl, heterocycloalkyl, aralkyl or heteroaralkyl radical;

the radicals $R^6$ and $R^7$, independently of one another, are a hydrogen atom, or an alkyl, alkenyl, alkinyl, heteroalkyl, aryl, heteroaryl, cycloalkyl, alkylcycloalkyl, heteroalkylcycloalkyl, heterocycloalkyl, aralkyl or heteroaralkyl radical; and X is a group of formula —CS—NHOH, —CH$_2$—CO—CH$_2$—OH, —CO—CH$_2$—OH, —CO—NHOH, —CNH—NHOH, —CH$_2$—NOH—CHS, —NOH—CHS, —NOH—CHO, —CH$_2$—NOH—CHO, —CH$_2$—CHOH—CHO, —CHOH—CHO, —CHOH—COOH, —CH(CH$_2$—OH)—COOH, —COOH or —CH$_2$COOH, or is selected from the following formulae:

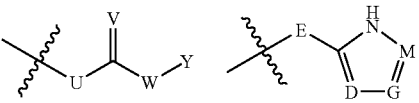

whereby U is a bond, CH$_2$, NH, O or S, V is O, S, NH or CH$_2$, W is O, S, NH or CH$_2$, and Y is OH or NH$_2$, E is a bond, CH$_2$, NH, O or S and the groups D, G and M, independently of one another, are N or CH, or a pharmaceutically acceptable salt, solvate, hydrate or a pharmaceutically acceptable formulation thereof.

The expression alkyl refers to a saturated, straight-chained or branched hydrocarbon group, which has in particular 1 to 20 carbon atoms, preferably 1 to 12 carbon atoms, most preferably 1 to 6 carbon atoms, e.g. the methyl, ethyl, propyl, isopropyl, n-butyl, isobutyl, tert-butyl, n-hexyl, 2,2-dimethylbutyl or n-octyl group.

The expressions alkenyl and alkinyl refer to at least partly unsaturated, straight-chained or branched hydrocarbon groups, which have in particular 2 to 20 carbon atoms, preferably 2 to 12 carbon atoms, most preferably 2 to 6 carbon atoms, e.g. the ethenyl, allyl, acetylenyl, propargyl, isoprenyl or hex-2-enyl group. Alkenyl groups preferably have one or two (most preferably one) double bond(s) and the alkinyl groups have one or two (most preferably one) triple bond(s).

In addition, the expressions alkyl, alkenyl and alkinyl refer to groups, in which e.g. one or more hydrogen atoms are replaced by a halogen atom (preferably F or Cl), —COOH, —OH, —SH, —NH$_2$, —NO$_2$, =O, =S, =NH, such as the 2,2,2-trichloroethyl or the trifluoromethyl group.

The expression heteroalkyl refers to an alkyl, alkenyl or alkinyl group, in which one or more (preferably 1, 2 or 3) carbon atoms are replaced by an oxygen, nitrogen, phosphorus, boron, selenium, silicon or sulfur atom (preferably oxygen, sulfur or nitrogen). The expression heteroalkyl refers furthermore to a carboxylic acid or a group derived from a carboxylic acid, such as acyl, acylalkyl, alkoxycarbonyl, acyloxy, acyloxyalkyl, carboxyalkylamide or alkoxycarbonyloxy.

Examples of heteroalkyl groups are groups of formulae $R^a$—O—$Y^a$—, $R^a$—S—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, whereby $R^a$ is a hydrogen atom, a $C_1$-$C_6$-alkyl-, a $C_2$-$C_6$-alkenyl- or a $C_2$-$C_6$-alkinyl group; $R^b$ is a hydrogen atom, a $C_1$-$C_6$-alkyl-, a $C_2$-$C_6$-alkenyl- or a $C_2$-$C_6$-alkinyl group; $R^c$ is a hydrogen atom, a $C_1$-$C_6$-alkyl-, a $C_2$-$C_6$-alkenyl- or a $C_2$-$C_6$-alkinyl group; $R^d$ is a hydrogen atom, a $C_1$-$C_6$-alkyl-, a $C_2$-$C_6$-alkenyl- or a $C_2$-$C_6$-alkinyl group and $Y^a$ is a direct bond, a $C_1$-$C_6$-alkylene, a $C_2$-$C_6$-alkenylene or a $C_2$-$C_6$-alkinylene group, whereby each heteroalkyl group contains at least one carbon atom and one or more hydrogen atoms can be replaced by fluorine or chlorine atoms. Specific examples of heteroalkyl groups are methoxy, trifluoromethoxy, ethoxy, n-propyloxy, isopropyloxy, tert-butyloxy, methoxymethyl, ethoxymethyl, methoxyethyl, methylamino, ethylamino, dimethylamino, diethylamino, iso-propylethylamino, methyl-aminomethyl, ethylaminomethyl, di-iso-propylaminoethyl, enolether, dimethylaminomethyl, dimethylaminoethyl, acetyl, propionyl, butyryloxy, acetyloxy, methoxycarbonyl, ethoxy-carbonyl, N-ethyl-N-methylcarbamoyl or N-methylcarbamoyl. Further examples of heteroalkyl groups are nitrile, isonitrile, cyanate, thiocyanate, isocyanate, isothiocyanate and alkylnitrile groups.

The expression cycloalkyl refers to a saturated or partially unsaturated (e.g. cycloalkenyl) cyclic group, which contains one or more rings (preferably 1 or 2), with in particular 3 to 14 ring carbon atoms, preferably 3 to 10 (especially 3, 4, 5, 6 or 7) ring carbon atoms. The expression cycloalkyl further refers to groups in which one or more hydrogen atoms are replaced by fluorine, chlorine, bromine or iodine atoms or —COOH, —OH, =O, —SH, =S, —NH$_2$, =NH or —NO$_2$ groups, that is, for example, cyclic ketones such as cyclohexanone, 2-cyclohexenone or cyclopentanone. Further specific examples of cycloalkyl groups are the cyclopropyl, cyclobutyl, cyclopentyl, spiro[4,5]decanyl, norbornyl, cyclohexyl, cyclopentenyl, cyclohexadienyl, decalinyl, cubanyl, bicyclo[4.3.0]nonyl, tetraline, cyclopentylcyclohexyl, fluorocyclohexyl or the cyclohex-2-enyl group.

The expression heterocycloalkyl refers to a cycloalkyl group as defined above, in which one or more (preferably 1, 2 or 3) ring carbon atoms are replaced by an oxygen, nitrogen, silicon, selenium, phosphorus or sulfur atom (preferably oxygen, sulfur or nitrogen). A heterocycloalkyl group preferably possesses 1 or 2 rings with 3 to 10 (especially 3, 4, 5, 6 or 7) ring atoms. The expression heterocycloalkyl further refers to groups in which one or more hydrogen atoms are replaced by fluorine, chlorine, bromine or iodine atoms or —COOH, —OH, =O, —SH, =S, —NH$_2$, =NH or —NO$_2$ groups. Examples are the piperidyl, morpholinyl, urotropinyl, pyrrolidinyl, tetrahydrothiophenyl, tetrahydropyranyl, tetrahydrofuryl, oxacyclopropyl, azacyclopropyl or 2-pyrazolinyl group, as well as lactams, lactones, cyclic imides and cyclic anhydrides.

The expression alkylcycloalkyl refers to group which, in accordance with the above definitions, contain both cycloalkyl and alkyl, alkenyl or alkinyl groups, e.g. alkylcycloalkyl, alkylcycloalkenyl, alkenylcycloalkyl and alkinylcycloalkyl groups. An alkylcycloalkyl group preferably contains a cycloalkyl group which has one or two rings with 3 to 10 (especially 3, 4, 5, 6 or 7) ring carbon atoms, and one or two alkyl, alkenyl or alkinyl groups with 1 or 2 to 6 carbon atoms.

The expression heteroalkylcycloalkyl refers to alkylcycloalkyl groups as defined above, in which one or more (preferably 1, 2 or 3) ring carbon atoms and/or carbon atoms are replaced by an oxygen, nitrogen, silicon, selenium, phosphorus or sulfur atom (preferably oxygen, sulfur or nitrogen). A heteroalkylcycloalkyl group preferably possesses 1 or 2 rings with 3 to 10 (especially 3, 4, 5, 6 or 7) ring atoms and one or two alkyl, alkenyl, alkinyl or heteroalkyl groups with 1 or 2 to 6 carbon atoms. Examples of such groups are alkylheterocycloalkyl, alkylheterocycloalkenyl, alkenylheterocycloalkyl, alkinylheterocycloalkyl, heteroalkylcycloalkyl, heteroalkylheterocycloalkyl and hetero-alkylheterocyclcoalkenyl, whereby the cyclic groups are saturated or are mono-, di- or tri-unsaturated.

The expression aryl or Ar refers to an aromatic group, which has one or more rings with in particular 6 to 14 ring carbon atoms, preferably 6 to 10 (especially 6) ring carbon atoms. The expression aryl (or Ar) further refers to groups in which one or more hydrogen atoms are replaced by fluorine, chlorine, bromine or iodine atoms or —COOH, —OH, —SH, —NH$_2$, or —NO$_2$ groups. Examples are the phenyl, naphthyl, biphenyl, 2-fluorophenyl, anilinyl, 3-nitrophenyl or 4-hydroxyphenyl group.

The expression heteroaryl refers to an aromatic group which contains one or more rings with in particular 5 to 14 ring atoms, preferably 5 to 10 (especially 5 or 6) ring atoms, and one or more (preferably 1, 2, 3 or 4) oxygen, nitrogen, phosphorus or sulfur ring atoms (preferably O, S or N). The expression heteroaryl further refers to groups in which one or more hydrogen atoms are replaced by fluorine, chlorine, bromine or iodine atoms or —COOH, —OH, —SH, —NH$_2$ or —NO$_2$ groups. Examples are 4-pyridyl, 2-imidazolyl, 3-phenylpyrrolyl, thiazolyl, oxazolyl, triazolyl, tetrazolyl, isoxazolyl, indazolyl, indolyl, benzimidazolyl, pyridazinyl, quinolinyl, purinyl, carbazolyl, acridinyl, pyrimidyl, 2,3-bifuryl, 3-pyrazolyl and isoquinolinyl groups.

The expression aralkyl refers to groups which, in accordance with the above definitions, contain both aryl and alkyl, alkenyl, alkinyl and/or cycloalkyl groups, such as arylalkyl, alkylaryl, arylalkenyl, arylalkinyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetraline, dihydronaphthalene, indanone, phenylcyclopentyl, cumene, cyclohexylphenyl, fluorene and indane. An aralkyl group preferably contains one or two aromatic rings with 6 to 10 ring carbon atoms and one or two alkyl, alkenyl and/or alkinyl groups with 1 or 2 to 6 carbon atoms and/or a cycloalkyl group with 5 or 6 ring carbon atoms.

The expression heteroaralkyl refers to an aralkyl group as defined above, in which one or more (preferably 1, 2, 3 or 4) ring carbon atoms and/or carbon atoms are replaced by an oxygen, nitrogen, silicon, selenium, phosphorus, boron or sulfur atom (preferably oxygen, sulfur or nitrogen), i.e. it refers to groups which, in accordance with the above definitions, contain both aryl or heteroaryl, and alkyl, alkenyl, alkinyl and/or heteroalkyl and/or cycloalkyl and/or heterocycloalkyl groups. A heteroaralkyl group preferably contains one or two aromatic rings with 5 or 6 to 10 ring carbon atoms and one or two alkyl, alkenyl and/or alkinyl groups with 1 or 2 to 6 carbon atoms and/or a cycloalkyl group with 5 or 6 ring carbon atoms, whereby 1, 2, 3 or 4 of these carbon atoms are replaced by oxygen, sulfur or nitrogen atoms.

Examples are arylheteroalkyl, arylheterocycloalkyl, arylheterocycloalkenyl, arylalkylheterocycloalkyl, arylalkenylheterocycloalkyl, arylalkinylheterocycloalkyl, aryl-alkylheterocycloalkenyl, heteroarylalkyl, heteroarylalkenyl, heteroarylalkinyl, heteroarylheteroalkyl, heteroarylcycloalkyl, heteroarylcycloalkenyl, heteroarylhetero-cycloalkyl, heteroarylheterocycloalkenyl, heteroarylalkylcycloalkyl, heteroarylalkylheterocycloalkyl, heteroarylheteroalkylcycloalkyl, heteroarylheteroalkyl-cycloalkenyl and heteroarylheteroalkylheterocycloalkyl groups, whereby the cyclic groups are saturated or are mono- di- or tri-unsaturated. Specific examples are the tetrahydroisoquinolinyl, benzoyl, 2- or 3-ethylindolyl, 4-methylpyridino, 2-, 3- or 4-methoxyphenyl, 4-ethoxyphenyl, 2-, 3- or 4-carboxyphenylalkyl group.

The expressions cycloalkyl, hereocycloalkyl, alkylcycloalkyl, heteroalkylcycloalkyl, aryl, heteroaryl, aralkyl and heteroaralky further refer to groups in which one or more hydrogen atoms are replaced by fluorine, chlorine, bromine or iodine atoms or OH, =O, SH, =S, $NH_2$, =NH or $NO_2$ groups.

The expression "optionally substituted" refers to groups in which one or more hydrogen atoms are replaced e.g. by fluorine, chlorine, bromine or iodine atoms or —COOH, —OH, =O, —SH, =S, —$NH_2$, =NH or —$NO_2$ groups. This expression further refers to groups that are substituted by unsubstituted $C_1$-$C_6$ alkyl, $C_2$-$C_6$ alkenyl, $C_2$-$C_6$ alkinyl, $C_1$-$C_6$ heteroalkyl, $C_3$-$C_{10}$ cycloalkyl, $C_2$-$C_9$ heterocycloalkyl, $C_6$-$C_{10}$ aryl, $C_1$-$C_9$ heteroaryl, $C_7$-$C_{12}$ aralkyl or $C_2$-$C_{11}$ heteroaralkyl groups.

Compounds of formula (I) may contain one or more centres of chirality depending on their substitution. The present invention therefore includes both all pure enantiomers and all pure diastereoisomers, and their mixtures in any ratio. In addition, the present invention also includes all cis/trans isomers of the compounds of the general formula (I) as well as mixtures thereof. In addition, the present invention includes all tautomeric forms of the compounds of formula (I).

Preference is given to compounds of formula (I), whereby W is NH and V is O, S or NH, Further preference is given to compounds of formula (I), whereby one, two or three of groups D, G and M are nitrogen atoms.

Particular preference is given to compounds of formula (I), whereby X is a group of formula —$CH_2$—CO—NHOH, —CO—NHOH, —$CH_2$—NOH—CHS, —NOH—CHS, —$CH_2$—NOH—CHO, —NOH—CHO, —$CH_2$—CO—$CH_2$OH, —CO—$CH_2$OH, —$CH_2$—CHOH—CHO, —CHOH—CHO or a group having one of the following formulae:

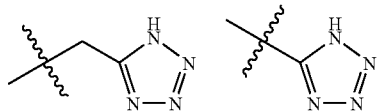

X is most preferably a group of formula —CO—NHOH.

In addition, $R^1$ is preferably a hydrogen atom, a chlorine atom, a bromine atom, an amino group, a methyl group or an ethyl group; especially a hydrogen atom or an amino group.

$R^2$ is more preferably a hydrogen atom, a chlorine atom, a bromine atom, a methyl group or an ethyl group; especially a hydrogen atom.

Furthermore, $R^3$ and $R^4$ are preferably not hydrogen atoms at the same time.

$R^3$ is more preferably a hydrogen atom, a chlorine atom, a bromine atom, an amino group, a methyl group, an ethyl group or a propyl group, especially a chlorine atom, a bromine atom or an amino group.

$R^4$ is, in turn, preferably a chlorine atom, a bromine atom, a methyl group, an ethyl group or a propyl group; especially a chlorine atom or a bromine atom.

Compounds of formula (I), in which $R^3$ is a bromine atom and $R^4$ is a methyl group, or in which $R^3$ is a hydrogen atom and $R^4$ is a chlorine atom or a bromine atom, are especially preferred.

More preferably, two of radicals $R^1$, $R^2$, $R^3$ and $R^4$ together are part of a cycloalkyl, heterocycloalkyl, aryl or heteroaryl ring, whereby each of these rings may optionally be substituted.

$R^5$ is, in turn, preferably a tert.-butyl group, an isopropyl group, a neopentyl group or a n-hexyl group; especially a tert.-butyl, neopentyl or n-hexyl group.

More preferably, the groups $R^6$ and $R^7$, independently of one another, are hydrogen atoms, hydroxymethyl or methyl groups.

Examples of pharmacologically acceptable salts of compounds of formula (I) are salts of physiologically acceptable mineral acids, such as hydrochloric acid, sulfuric acid and phosphoric acid; or salts of organic acids, such as methanesulfonic acid, p-toluene-sulfonic acid, lactic acid, formic acid, acetic acid, trifluoroacetic acid, citric acid, succinic acid, fumaric acid, maleic acid and salicylic acid. Compounds of formula (I) may be solvated, in particular hydrated. Hydration may arise e.g. during the preparation process or as a consequence of the hygroscopic nature of the initially water-free compounds of formula (I).

The pharmaceutical compositions according to the present invention contain at least one compound of formula (I) as active ingredient and optionally carriers and/or adjuvants.

The prodrugs (for definition and examples see e.g. R. B. Silverman, Medizinische Chemie, VCH Weinheim, 1995, chapter 8, pp 361ff), which are likewise an object of the present invention, contain a compound of formula (I) and at least one pharmacologically acceptable protecting group, which is cleaved under physiological conditions, e.g. a hydroxy, alkoxy, aralkyloxy, acyl or acyloxy group, such as a methoxy, ethoxy, benzyloxy, acetyl or acetyloxy group.

The therapeutical usage of the compounds of formula (I), their pharmacologically acceptable salts or solvates and hydrates, as well as formulations and pharmaceutical compositions, is likewise an object of the present invention.

Compounds of formula (I) are of great interest especially as inhibitors of metalloproteinases (in particular PDF). The usage of these active ingredients in the production of medicaments to prevent and/or treat diseases, especially those conveyed by PDF, is also an object of the present invention. In general, compounds of formula (I) are administered using known, acceptable methods, either singly or in combination with any other therapeutic agent. Administration may be effected e.g. in one of the following ways: orally, e.g. as dragées, coated tablets, pills, semi-solids, soft or hard capsules, solutions, emulsions or suspensions; parenterally, e.g. as an injectable solution; rectally as suppositories; by inhalation, e.g. as a powder formulation or spray, transdermally or intra-nasally. To produce such tablets, pills, semi-solids, coated tablets, dragées and hard gelatin capsules, the therapeutically employable product may be mixed with pharmacologically inert, inorganic or organic carriers for medicaments, e.g. with lactose, sucrose, glucose, gelatin, malt, silica gel, starch or derivatives thereof, talc, stearic acid or salts thereof, dry skimmed milk and the like. To produce soft capsules, carriers for medicaments, such as vegetable oils, petroleum, animal or synthetic oils, wax, fat, polyols, may be used. To produce liquid solutions and syrups, carriers for medicaments, such as water, alcohols, aqueous salt solution, aqueous dextrose, polyols, glycerol, vegetable oils, petroleum, animal or synthetic oils, may be used. For suppositories, carriers for medicaments, such as vegetable oils, petroleum, animal or synthetic oils, wax, fat and polyols, may be used. For aerosol formulations, compressed gases that are appropriate for this purpose may be used, such as oxygen, nitrogen and carbon dioxide. The pharmaceutically acceptable agents may also contain preserving and stabilizing additives, emulsifiers, sweeteners, aromatics, salts to modify the osmotic pressure, buffers, coating additives and antioxidants.

Compounds of formula (I) with X=—COOCH₃ may be produced by reacting compounds of formulae (II), (III) and (IV), in which the radicals are defined as above.

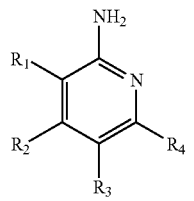
(II)

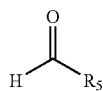
(III)

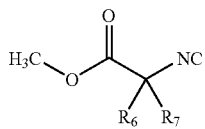
(IV)

By reacting the reaction product with hydroxylamine in methanol, compounds of formula (I) with X=—CO—NHOH may be produced.

EXAMPLES

General Procedure

50 μl of a 0.2 M solution of amine (II) in methanol were dispensed onto a 96-well plate (amines that are insoluble in methanol were dispensed manually). 50 μl of a 0.2 M solution of the aldehyde (III) in methanol were added. The plate was shaken for 2 h at room temperature. Subsequently, 50 μl of a 0.2 M solution of the isocyanide (IV) in methanol and 50 μl of a 0.4 M acetic acid solution in methanol were dispensed. The plate was shaken over night at room temperature, the solvent evaporated, and the residue dissolved in 150 μl of a 0.5 M NH₂OH solution in methanol. The plate was again shaken over night at room temperature.

The following compounds were produced in accordance with the general procedure, using appropriate starting materials, and were identified by mass spectrometry. All compounds were investigated for their activity as PDF inhibitors (for the assay, see D. Chen et al. Antimicrobial Agents and Chemotherapy, January 2004, pp. 250-261) and had IC$_{50}$ values ranging between 1 nmol and 50 μmol.

| Example | calc. [M + H] | found [M + H] |
|---|---|---|
| 2-(6-fluoro-imidazo[1,2-a]pyridin-3-ylamino)-N-hydroxy-acetamide | 225.09 | 225.08 |
| 2-(6-bromo-8-methyl-imidazo[1,2-a]pyridin-3-ylamino)-N-hydroxy-acetamide | 299.03 | 299.04 |
| 2-(6-bromo-2,5-dimethyl-imidazo[1,2-a]pyridin-3-ylamino)-N-hydroxy-acetamide | 313.05 | 313.08 |
| N-hydroxy-2-(6-iodo-2-isobutyl-imidazo[1,2-a]pyridin-3-ylamino)-acetamide | 389.07 | 389.10 |
| 2-(6-bromo-2,5-dimethyl-imidazo[1,2-a]pyridin-3-ylamino)-N-hydroxy-propionamide | 327.07 | 327.10 |
| 2-(2-tert-butyl-6-iodo-imidazo[1,2-a]pyridin-3-ylamino)-N-hydroxy-acetamide | 389.07 | 389.11 |
| 2-(6-bromo-2-ethyl-5-methyl-imidazo[1,2-a]pyridin-3-ylamino)-N-hydroxy-acetamide | 327.07 | 327.10 |
| 2-(6-chloro-2-cyclopropyl-imidazo[1,2-a]pyridin-3-ylamino)-N-hydroxy-propionamide | 295.12 | 295.14 |
| 2-(6-chloro-2-isopropyl-imidazo[1,2-a]pyridin-3-ylamino)-N-hydroxy-propionamide | 297.14 | 297.18 |
| 2-(6-bromo-2-ethyl-5-methyl-imidazo[1,2-a]pyridin-3-ylamino)-N-hydroxy-propionamide | 341.09 | 341.12 |
| 2-(6-bromo-2-isopropyl-5-methyl-imidazo[1,2-a]pyridin-3-ylamino)-N-hydroxy-acetamide | 341.09 | 341.12 |
| 2-[6-bromo-5-methyl-2-((E)-propenyl)-imidazo[1,2-a]pyridin-3-ylamino]-N-hydroxy-acetamide | 339.07 | 339.11 |
| 2-(6-chloro-2-isobutyl-imidazo[1,2-a]pyridin-3-ylamino)-N-hydroxy-acetamide | 297.14 | 297.17 |
| 2-(2-tert-butyl-6-chloro-imidazo[1,2-a]pyridin-3-ylamino)-N-hydroxy-acetamide | 297.14 | 297.16 |
| 2-(2-tert-butyl-6-chloro-imidazo[1,2-a]pyridin-3-ylamino)-N-hydroxy-propionamide | 311.16 | 311.23 |
| 2-(2-tert-butyl-6-fluoro-imidazo[1,2-a]pyridin-3-ylamino)-N-hydroxy-acetamide | 281.17 | 281.15 |
| 2-(6-fluoro-2-isobutyl-imidazo[1,2-a]pyridin-3-ylamino)-N-hydroxy-acetamide | 281.17 | 281.19 |
| N-hydroxy-2-(2-isobutyl-5-methyl-imidazo[1,2-a]pyridin-3-ylamino)-acetamide | 277.20 | 277.21 |
| 2-(6-bromo-5-methyl-2-propyl-imidazo[1,2-a]pyridin-3-ylamino)-N-hydroxy-acetamide | 341.09 | 341.12 |
| 2-(6-bromo-2-isobutyl-5-methyl-imidazo[1,2-a]pyridin-3-ylamino)-N-hydroxy-acetamide | 355.11 | 355.14 |
| 2-(2-tert-butyl-6-methyl-imidazo[1,2-a]pyridin-3-ylamino)-N-hydroxy-acetamide | 277.20 | 277.20 |

-continued

| Example | calc. [M + H] | found [M + H] |
|---|---|---|
| N-hydroxy-2-(6-iodo-2-isobutyl-imidazo[1,2-a]pyridin-3-ylamino)-propionamide | 403.09 | 403.12 |
| 2-(6-bromo-8-methyl-2-propyl-imidazo[1,2-a]pyridin-3-ylamino)-N-hydroxy-propionamide | 355.11 | 355.08 |
| 2-(6-bromo-2-tert-butyl-5-methyl-imidazo[1,2-a]pyridin-3-ylamino)-N-hydroxy-acetamide | 355.11 | 355.13 |
| 2-(6-chloro-2-propyl-imidazo[1,2-a]pyridin-3-ylamino)-N-hydroxy-propionamide | 297.14 | 297.16 |
| 2-(2-tert-butyl-6-methyl-imidazo[1,2-a]pyridin-3-ylamino)-N-hydroxy-propionamide | 291.22 | 291.22 |
| 2-(6-chloro-2-isobutyl-imidazo[1,2-a]pyridin-3-ylamino)-N-hydroxy-propionamide | 311.16 | 311.17 |
| 2-(6-bromo-5-methyl-2-propyl-imidazo[1,2-a]pyridin-3-ylamino)-N-hydroxy-propionamide | 355.11 | 355.13 |
| 2-(6-bromo-2-tert-butyl-5-methyl-imidazo[1,2-a]pyridin-3-ylamino)-N-hydroxy-propionamide | 369.13 | 369.16 |
| 2-(6-bromo-2-isobutyl-8-methyl-imidazo[1,2-a]pyridin-3-ylamino)-N-hydroxy-propionamide | 369.13 | 369.15 |
| 2-(6-bromo-2-isobutyl-5-methyl-imidazo[1,2-a]pyridin-3-ylamino)-N-hydroxy-propionamide | 369.13 | 369.15 |
| N-hydroxy-2-(2-hydroxymethyl-5-methyl-imidazo[1,2-a]pyridin-3-ylamino)-acetamide | 251.14 | 251.15 |
| 2-(5-ethyl-2-hydroxymethyl-imidazo[1,2-a]pyridin-3-ylamino)-N-hydroxy-acetamide | 265.16 | 265.17 |
| 2-(5-ethyl-2-methyl-imidazo[1,2-a]pyridin-3-ylamino)-N-hydroxy-acetamide | 249.16 | 249.17 |
| N-hydroxy-2-[2-(1H-imidazol-2-yl)-5-methyl-imidazo[1,2-a]pyridin-3-ylamino]-acetamide | 287.15 | 287.16 |
| 2-(2,5-diethyl-imidazo[1,2-a]pyridin-3-ylamino)-N-hydroxy-acetamide | 263.18 | 263.19 |
| 2-[5-ethyl-2-(1H-imidazol-2-yl)-imidazo[1,2-a]pyridin-3-ylamino]-N-hydroxy-acetamide | 301.16 | 301.18 |
| 2-(5-ethyl-2-hydroxymethyl-imidazo[1,2-a]pyridin-3-ylamino)-N-hydroxy-propionamide | 279.17 | 279.26 |
| 2-[5-ethyl-2-((E)-propenyl)-imidazo[1,2-a]pyridin-3-ylamino]-N-hydroxy-acetamide | 275.18 | 0.00 |
| 2-[7-ethyl-2-(1H-imidazol-2-yl)-imidazo[1,2-a]pyridin-3-ylamino]-N-hydroxy-acetamide | 301.16 | 301.18 |
| 2-(2-furan-2-yl-5-methyl-imidazo[1,2-a]pyridin-3-ylamino)-N-hydroxy-acetamide | 287.13 | 287.15 |
| N-hydroxy-2-[8-methyl-2-(1H-pyrazol-3-yl)-imidazo[1,2-a]pyridin-3-ylamino]-acetamide | 287.15 | 287.16 |
| 2-(2-cyclopropyl-5-ethyl-imidazo[1,2-a]pyridin-3-ylamino)-N-hydroxy-acetamide | 275.18 | 275.18 |
| N-hydroxy-2-(8-hydroxy-2-methyl-imidazo[1,2-a]pyridin-3-ylamino)-3-phenyl-propionamide | 327.17 | 327.10 |
| N-hydroxy-2-(5-methyl-2-phenyl-imidazo[1,2-a]pyridin-3-ylamino)-acetamide | 297.16 | 297.17 |
| N-hydroxy-2-(7-methyl-imidazo[1,2-a]pyridin-3-ylamino)-3-phenyl-propionamide | 311.18 | 311.15 |
| 2-(2-butyl-5-propyl-imidazo[1,2-a]pyridin-3-ylamino)-N-hydroxy-acetamide | 305.24 | 305.22 |
| 2-(2-ethyl-5-propyl-imidazo[1,2-a]pyridin-3-ylamino)-N-hydroxy-acetamide | 277.20 | 277.19 |
| N-hydroxy-2-(2-isobutyl-5-propyl-imidazo[1,2-a]pyridin-3-ylamino)-acetamide | 305.24 | 305.14 |
| N-hydroxy-2-(2-hydroxymethyl-5-propyl-imidazo[1,2-a]pyridin-3-ylamino)-acetamide | 279.17 | 279.17 |
| 2-(2-benzyl-5-propyl-imidazo[1,2-a]pyridin-3-ylamino)-N-hydroxy-acetamide | 339.22 | 339.22 |
| N-hydroxy-2-(2-pentyl-5-propyl-imidazo[1,2-a]pyridin-3-ylamino)-acetamide | 319.26 | 319.25 |
| N-hydroxy-2-(2-methyl-5-propyl-imidazo[1,2-a]pyridin-3-ylamino)-acetamide | 263.18 | 263.17 |
| 3-[3-(hydroxycarbamoylmethyl-amino)-5-propyl-imidazo[1,2-a]pyridin-2-yl]-propionic acid | 321.19 | 321.18 |
| 2-(2,5-dipropyl-imidazo[1,2-a]pyridin-3-ylamino)-N-hydroxy-acetamide | 291.22 | 291.21 |
| N-hydroxy-2-[2-(2-methylsulfanyl-ethyl)-5-propyl-imidazo[1,2-a]pyridin-3-ylamino]-acetamide | 323.19 | 323.18 |
| 2-(2-tert-butyl-5-propyl-imidazo[1,2-a]pyridin-3-ylamino)-N-hydroxy-acetamide | 305.24 | 305.22 |
| 2-[2-(2,2-dimethyl-propyl)-5-propyl-imidazo[1,2-a]pyridin-3-ylamino]-N-hydroxy-acetamide | 319.26 | 319.25 |
| 2-(2-hept-1-inyl-5-propyl-imidazo[1,2-a]pyridin-3-ylamino)-N-hydroxy-acetamide | 343.26 | 343.25 |

-continued

| Example | calc. [M + H] | found [M + H] |
|---|---|---|
| N-hydroxy-2-(2-pentyl-6-trifluoromethyl-imidazo[1,2-a]pyridin-3-ylamino)-acetamide | 345.18 | 345.20 |
| 2-[2-(2,2-dimethyl-propyl)-6-trifluoromethyl-imidazo[1,2-a]pyridin-3-ylamino]-N-hydroxy-acetamide | 345.18 | 345.20 |
| 2-(2-hept-1-inyl-6-trifluoromethyl-imidazo[1,2-a]pyridin-3-ylamino)-N-hydroxy-acetamide | 369.18 | 369.11 |
| 2-(6-fluoro-2-pentyl-imidazo[1,2-a]pyridin-3-ylamino)-N-hydroxy-acetamide | 295.19 | 295.20 |
| 2-[2-(2,2-dimethyl-propyl)-6-fluoro-imidazo[1,2-a]pyridin-3-ylamino]-N-hydroxy-acetamide | 295.19 | 295.19 |
| 2-(2-butyl-5-methyl-imidazo[1,2-a]pyridin-3-ylamino)-N-hydroxy-acetamide | 277.20 | 277.19 |
| 2-(2-benzyl-5-methyl-imidazo[1,2-a]pyridin-3-ylamino)-N-hydroxy-acetamide | 311.18 | 311.19 |
| N-hydroxy-2-(5-methyl-2-pentyl-imidazo[1,2-a]pyridin-3-ylamino)-acetamide | 291.22 | 291.22 |
| N-hydroxy-2-[5-methyl-2-(2-methylsulfanyl-ethyl)-imidazo[1,2-a]pyridin-3-ylamino]-acetamide | 295.15 | 295.09 |
| 2-(2-tert-butyl-5-methyl-imidazo[1,2-a]pyridin-3-ylamino)-N-hydroxy-acetamide | 277.20 | 277.21 |
| 2-[2-(2,2-dimethyl-propyl)-5-methyl-imidazo[1,2-a]pyridin-3-ylamino]-N-hydroxy-acetamide | 291.22 | 291.22 |
| 2-(2-hept-1-inyl-5-methyl-imidazo[1,2-a]pyridin-3-ylamino)-N-hydroxy-acetamide | 315.22 | 315.23 |
| 2-(2-butyl-imidazo[1,2-a]quinolin-1-ylamino)-N-hydroxy-acetamide | 313.20 | 313.21 |
| 2-(2-benzyl-imidazo[1,2-a]quinolin-1-ylamino)-N-hydroxy-acetamide | 347.18 | 347.20 |
| N-hydroxy-2-(2-pentyl-imidazo[1,2-a]quinolin-1-ylamino)-acetamide | 327.22 | 327.23 |
| N-hydroxy-2-(2-propyl-imidazo[1,2-a]quinolin-1-ylamino)-acetamide | 299.18 | 299.21 |
| N-hydroxy-2-[2-(2-methylsulfanyl-ethyl)-imidazo[1,2-a]quinolin-1-ylamino]-acetamide | 331.15 | 331.18 |
| 2-(2-tert-butyl-imidazo[1,2-a]quinolin-1-ylamino)-N-hydroxy-acetamide | 313.20 | 313.21 |
| 2-[2-(2,2-dimethyl-propyl)-imidazo[1,2-a]quinolin-1-ylamino]-N-hydroxy-acetamide | 327.22 | 327.23 |
| 2-(2-hept-1-inyl-imidazo[1,2-a]quinolin-1-ylamino)-N-hydroxy-acetamide | 351.22 | 351.23 |
| 2-(6-bromo-2-isobutyl-8-methyl-imidazo[1,2-a]pyridin-3-ylamino)-N-hydroxy-acetamide | 355.11 | 355.03 |
| 2-[6-bromo-2-(2,2-dimethyl-propyl)-8-methyl-imidazo[1,2-a]pyridin-3-ylamino]-N-hydroxy-acetamide | 369.13 | 369.15 |
| 2-(6-bromo-2-hept-1-inyl-8-methyl-imidazo[1,2-a]pyridin-3-ylamino)-N-hydroxy-acetamide | 393.13 | 393.14 |
| 2-(6-chloro-2-pentyl-imidazo[1,2-a]pyridin-3-ylamino)-N-hydroxy-acetamide | 311.16 | 311.17 |
| 2-[6-chloro-2-(2,2-dimethyl-propyl)-imidazo[1,2-a]pyridin-3-ylamino]-N-hydroxy-acetamide | 311.16 | 311.17 |
| 2-(6-chloro-2-hept-1-inyl-imidazo[1,2-a]pyridin-3-ylamino)-N-hydroxy-acetamide | 335.16 | 335.17 |
| 2-(2-butyl-6-nitro-imidazo[1,2-a]pyridin-3-ylamino)-N-hydroxy-acetamide | 308.16 | 308.15 |
| N-hydroxy-2-(2-isobutyl-6-nitro-imidazo[1,2-a]pyridin-3-ylamino)-acetamide | 308.16 | 308.11 |
| 2-(2-benzyl-6-nitro-imidazo[1,2-a]pyridin-3-ylamino)-N-hydroxy-acetamide | 342.14 | 342.17 |
| N-hydroxy-2-(6-nitro-2-pentyl-imidazo[1,2-a]pyridin-3-ylamino)-acetamide | 322.18 | 322.19 |
| 2-[2-(2,2-dimethyl-propyl)-6-nitro-imidazo[1,2-a]pyridin-3-ylamino]-N-hydroxy-acetamide | 322.18 | 322.20 |
| 2-(2-hept-1-inyl-6-nitro-imidazo[1,2-a]pyridin-3-ylamino)-N-hydroxy-acetamide | 346.18 | 346.20 |
| 2-(2-butyl-6-methyl-imidazo[1,2-a]pyridin-3-ylamino)-N-hydroxy-acetamide | 277.20 | 277.18 |
| N-hydroxy-2-(6-methyl-2-pentyl-imidazo[1,2-a]pyridin-3-ylamino)-acetamide | 291.22 | 291.22 |
| 2-[2-(2,2-dimethyl-propyl)-6-methyl-imidazo[1,2-a]pyridin-3-ylamino]-N-hydroxy-acetamide | 291.22 | 291.22 |
| 2-(2-hept-1-inyl-6-methyl-imidazo[1,2-a]pyridin-3-ylamino)-N-hydroxy-acetamide | 315.22 | 315.22 |
| 2-(2-butyl-5,7-dimethyl-imidazo[1,2-a]pyridin-3-ylamino)-N-hydroxy-acetamide | 291.22 | 291.23 |
| N-hydroxy-2-(2-isobutyl-5,7-dimethyl-imidazo[1,2-a]pyridin-3-ylamino)-acetamide | 291.22 | 291.21 |

-continued

| Example | calc. [M + H] | found [M + H] |
|---|---|---|
| N-hydroxy-2-(2-hydroxymethyl-5,7-dimethyl-imidazo[1,2-a]pyridin-3-ylamino)-acetamide | 265.16 | 265.16 |
| 2-(2-benzyl-5,7-dimethyl-imidazo[1,2-a]pyridin-3-ylamino)-N-hydroxy-acetamide | 325.20 | 325.21 |
| 2-(5,7-dimethyl-2-pentyl-imidazo[1,2-a]pyridin-3-ylamino)-N-hydroxy-acetamide | 305.24 | 305.24 |
| 3-[3-(hydroxycarbamoylmethyl-amino)-5,7-dimethyl-imidazo[1,2-a]pyridin-2-yl]-propionic acid | 307.17 | 307.10 |
| 2-(5,7-dimethyl-2-propyl-imidazo[1,2-a]pyridin-3-ylamino)-N-hydroxy-acetamide | 277.20 | 277.26 |
| 2-[5,7-dimethyl-2-(2-methylsulfanyl-ethyl)-imidazo[1,2-a]pyridin-3-ylamino]-N-hydroxy-acetamide | 309.17 | 309.18 |
| 2-(2-tert-butyl-5,7-dimethyl-imidazo[1,2-a]pyridin-3-ylamino)-N-hydroxy-acetamide | 291.22 | 291.22 |
| 2-[2-(2,2-dimethyl-propyl)-5,7-dimethyl-imidazo[1,2-a]pyridin-3-ylamino]-N-hydroxy-acetamide | 305.24 | 305.24 |
| 2-(2-hept-1-inyl-5,7-dimethyl-imidazo[1,2-a]pyridin-3-ylamino)-N-hydroxy-acetamide | 329.24 | 329.24 |
| 2-(6,8-dibromo-2-butyl-imidazo[1,2-a]pyridin-3-ylamino)-N-hydroxy-acetamide | 419.00 | 419.03 |
| 2-(6,8-dibromo-2-isobutyl-imidazo[1,2-a]pyridin-3-ylamino)-N-hydroxy-acetamide | 419.00 | 419.03 |
| 2-(6,8-dibromo-2-hydroxymethyl-imidazo[1,2-a]pyridin-3-ylamino)-N-hydroxy-acetamide | 392.93 | 393.00 |
| 2-(2-benzyl-6,8-dibromo-imidazo[1,2-a]pyridin-3-ylamino)-N-hydroxy-acetamide | 452.97 | 453.02 |
| 2-(6,8-dibromo-2-pentyl-imidazo[1,2-a]pyridin-3-ylamino)-N-hydroxy-acetamide | 433.02 | 433.05 |
| 2-[6,8-dibromo-2-(2-methylsulfanyl-ethyl)-imidazo[1,2-a]pyridin-3-ylamino]-N-hydroxy-acetamide | 436.95 | 436.97 |
| 2-[6,8-dibromo-2-(2,2-dimethyl-propyl)-imidazo[1,2-a]pyridin-3-ylamino]-N-hydroxy-acetamide | 433.02 | 433.02 |
| 2-(6,8-dibromo-2-hept-1-inyl-imidazo[1,2-a]pyridin-3-ylamino)-N-hydroxy-acetamide | 457.01 | 457.03 |
| 2-(2-butyl-8-chloro-6-trifluoromethyl-imidazo[1,2-a]pyridin-3-ylamino)-N-hydroxy-acetamide | 365.12 | 365.14 |
| 2-(8-chloro-2-hydroxymethyl-6-trifluoromethyl-imidazo[1,2-a]pyridin-3-ylamino)-N-hydroxy-acetamide | 339.06 | 339.03 |
| 2-(2-benzyl-8-chloro-6-trifluoromethyl-imidazo[1,2-a]pyridin-3-ylamino)-N-hydroxy-acetamide | 399.10 | 399.15 |
| 2-(8-chloro-2-pentyl-6-trifluoromethyl-imidazo[1,2-a]pyridin-3-ylamino)-N-hydroxy-acetamide | 379.14 | 379.15 |
| 2-[8-chloro-2-(2,2-dimethyl-propyl)-6-trifluoromethyl-imidazo[1,2-a]pyridin-3-ylamino]-N-hydroxy-acetamide | 379.14 | 379.15 |
| 2-(8-chloro-2-hept-1-inyl-6-trifluoromethyl-imidazo[1,2-a]pyridin-3-ylamino)-N-hydroxy-acetamide | 403.14 | 403.14 |
| 2-(6-bromo-2-isobutyl-imidazo[1,2-a]pyridin-3-ylamino)-N-hydroxy-acetamide | 341.09 | 341.09 |
| 2-(6-bromo-2-pentyl-imidazo[1,2-a]pyridin-3-ylamino)-N-hydroxy-acetamide | 355.11 | 355.10 |
| 2-(6-bromo-2-tert-butyl-imidazo[1,2-a]pyridin-3-ylamino)-N-hydroxy-acetamide | 341.09 | 341.09 |
| 2-[6-bromo-2-(2,2-dimethyl-propyl)-imidazo[1,2-a]pyridin-3-ylamino]-N-hydroxy-acetamide | 355.11 | 355.11 |
| 2-(6-bromo-2-hept-1-inyl-imidazo[1,2-a]pyridin-3-ylamino)-N-hydroxy-acetamide | 379.11 | 379.12 |
| 2-(2-butyl-9-hydroxy-imidazo[1,2-a]quinolin-1-ylamino)-N-hydroxy-acetamide | 329.19 | 329.19 |
| 2-(2-ethyl-9-hydroxy-imidazo[1,2-a]quinolin-1-ylamino)-N-hydroxy-acetamide | 301.15 | 301.16 |
| N-hydroxy-2-(9-hydroxy-2-isobutyl-imidazo[1,2-a]quinolin-1-ylamino)-acetamide | 329.19 | 329.19 |
| 2-(2-benzyl-9-hydroxy-imidazo[1,2-a]quinolin-1-ylamino)-N-hydroxy-acetamide | 363.17 | 363.18 |
| N-hydroxy-2-(9-hydroxy-2-pentyl-imidazo[1,2-a]quinolin-1-ylamino)-acetamide | 343.21 | 343.21 |
| N-hydroxy-2-(9-hydroxy-2-propyl-imidazo[1,2-a]quinolin-1-ylamino)-acetamide | 315.17 | 315.17 |
| N-hydroxy-2-[9-hydroxy-2-(2-methylsulfanyl-ethyl)-imidazo[1,2-a]quinolin-1-ylamino]-acetamide | 347.14 | 347.15 |
| 2-(2-tert-butyl-9-hydroxy-imidazo[1,2-a]quinolin-1-ylamino)-N-hydroxy-acetamide | 329.19 | 329.19 |
| 2-[2-(2,2-dimethyl-propyl)-9-hydroxy-imidazo[1,2-a]quinolin-1-ylamino]-N-hydroxy-acetamide | 343.21 | 343.21 |
| 2-(8-bromo-2-butyl-6-methyl-imidazo[1,2-a]pyridin-3-ylamino)-N-hydroxy-acetamide | 355.11 | 355.11 |

-continued

| Example | calc. [M + H] | found [M + H] |
|---|---|---|
| 2-(8-bromo-6-methyl-2-pentyl-imidazo[1,2-a]pyridin-3-ylamino)-N-hydroxy-acetamide | 369.13 | 369.12 |
| 2-[8-bromo-2-(2,2-dimethyl-propyl)-6-methyl-imidazo[1,2-a]pyridin-3-ylamino]-N-hydroxy-acetamide | 369.13 | 369.12 |
| 2-(8-bromo-2-hept-1-inyl-6-methyl-imidazo[1,2-a]pyridin-3-ylamino)-N-hydroxy-acetamide | 393.13 | 393.13 |
| 2-(2-butyl-5-chloro-imidazo[1,2-a]pyridin-3-ylamino)-N-hydroxy-acetamide | 297.14 | 297.14 |
| 2-(5-chloro-2-ethyl-imidazo[1,2-a]pyridin-3-ylamino)-N-hydroxy-acetamide | 269.10 | 269.14 |
| 2-(5-chloro-2-isobutyl-imidazo[1,2-a]pyridin-3-ylamino)-N-hydroxy-acetamide | 297.14 | 297.14 |
| 2-(5-chloro-2-hydroxymethyl-imidazo[1,2-a]pyridin-3-ylamino)-N-hydroxy-acetamide | 271.07 | 271.09 |
| 2-(2-benzyl-5-chloro-imidazo[1,2-a]pyridin-3-ylamino)-N-hydroxy-acetamide | 331.12 | 331.13 |
| 2-(5-chloro-2-pentyl-imidazo[1,2-a]pyridin-3-ylamino)-N-hydroxy-acetamide | 311.16 | 311.16 |
| 2-(5-chloro-2-methyl-imidazo[1,2-a]pyridin-3-ylamino)-N-hydroxy-acetamide | 255.08 | 255.09 |
| 3-[5-chloro-3-(hydroxycarbamoylmethyl-amino)-imidazo[1,2-a]pyridin-2-yl]-propionic acid | 313.09 | 313.13 |
| 2-(5-chloro-2-propyl-imidazo[1,2-a]pyridin-3-ylamino)-N-hydroxy-acetamide | 283.12 | 283.18 |
| 2-[5-chloro-2-(2-methylsulfanyl-ethyl)-imidazo[1,2-a]pyridin-3-ylamino]-N-hydroxy-acetamide | 315.09 | 315.10 |
| 2-(2-tert-butyl-5-chloro-imidazo[1,2-a]pyridin-3-ylamino)-N-hydroxy-acetamide | 297.14 | 297.14 |
| 2-[5-chloro-2-(2,2-dimethyl-propyl)-imidazo[1,2-a]pyridin-3-ylamino]-N-hydroxy-acetamide | 311.16 | 311.16 |
| 2-(5-chloro-2-hept-1-inyl-imidazo[1,2-a]pyridin-3-ylamino)-N-hydroxy-acetamide | 335.16 | 335.17 |
| N-hydroxy-2-(5-methyl-6-nitro-2-propyl-imidazo[1,2-a]pyridin-3-ylamino)-acetamide | 308.16 | 308.14 |
| 2-[2-(2,2-dimethyl-propyl)-5-methyl-6-nitro-imidazo[1,2-a]pyridin-3-ylamino]-N-hydroxy-acetamide | 336.20 | 336.25 |
| 2-(5-bromo-2-propyl-imidazo[1,2-b]isoquinolin-3-ylamino)-N-hydroxy-acetamide | 377.09 | 377.13 |
| 2-[5-bromo-2-(2-methylsulfanyl-ethyl)-imidazo[1,2-b]isoquinolin-3-ylamino]-N-hydroxy-acetamide | 409.06 | 409.08 |
| 2-(6,8-dibromo-2-butyl-5-methyl-imidazo[1,2-a]pyridin-3-ylamino)-N-hydroxy-acetamide | 433.02 | 433.05 |
| 2-(6,8-dibromo-2-ethyl-5-methyl-imidazo[1,2-a]pyridin-3-ylamino)-N-hydroxy-acetamide | 404.98 | 405.00 |
| 2-(6,8-dibromo-2-isobutyl-5-methyl-imidazo[1,2-a]pyridin-3-ylamino)-N-hydroxy-acetamide | 433.02 | 433.03 |
| 2-(6,8-dibromo-2-hydroxymethyl-5-methyl-imidazo[1,2-a]pyridin-3-ylamino)-N-hydroxy-acetamide | 406.95 | 406.98 |
| 2-(2-benzyl-6,8-dibromo-5-methyl-imidazo[1,2-a]pyridin-3-ylamino)-N-hydroxy-acetamide | 466.99 | 466.96 |
| 2-(6,8-dibromo-5-methyl-2-pentyl-imidazo[1,2-a]pyridin-3-ylamino)-N-hydroxy-acetamide | 447.03 | 447.04 |
| 2-(6,8-dibromo-2,5-dimethyl-imidazo[1,2-a]pyridin-3-ylamino)-N-hydroxy-acetamide | 390.96 | 390.98 |
| 2-(6,8-dibromo-5-methyl-2-propyl-imidazo[1,2-a]pyridin-3-ylamino)-N-hydroxy-acetamide | 419.00 | 419.01 |
| 2-[6,8-dibromo-5-methyl-2-(2-methylsulfanyl-ethyl)-imidazo[1,2-a]pyridin-3-ylamino]-N-hydroxy-acetamide | 450.97 | 451.02 |
| 2-[6,8-dibromo-2-(2,2-dimethyl-propyl)-5-methyl-imidazo[1,2-a]pyridin-3-ylamino]-N-hydroxy-acetamide | 447.03 | 447.05 |
| 2-(6,8-dibromo-2-hept-1-inyl-5-methyl-imidazo[1,2-a]pyridin-3-ylamino)-N-hydroxy-acetamide | 471.03 | 471.08 |
| 2-(2-butyl-5-hydroxy-imidazo[1,2-a]quinolin-1-ylamino)-N-hydroxy-acetamide | 329.19 | 329.20 |
| N-hydroxy-2-(5-hydroxy-2-isobutyl-imidazo[1,2-a]quinolin-1-ylamino)-acetamide | 329.19 | 329.20 |
| 2-(2-benzyl-5-hydroxy-imidazo[1,2-a]quinolin-1-ylamino)-N-hydroxy-acetamide | 363.17 | 363.17 |
| N-hydroxy-2-(5-hydroxy-2-pentyl-imidazo[1,2-a]quinolin-1-ylamino)-acetamide | 343.21 | 343.19 |
| N-hydroxy-2-(5-hydroxy-2-propyl-imidazo[1,2-a]quinolin-1-ylamino)-acetamide | 315.17 | 315.23 |
| N-hydroxy-2-[5-hydroxy-2-(2-methylsulfanyl-ethyl)-imidazo[1,2-a]quinolin-1-ylamino]-acetamide | 347.14 | 347.15 |
| 2-[2-(2,2-dimethyl-propyl)-5-hydroxy-imidazo[1,2-a]quinolin-1-ylamino]-N-hydroxy-acetamide | 343.21 | 343.21 |

-continued

| Example | calc. [M + H] | found [M + H] |
|---|---|---|
| 2-(2-butyl-6,8-difluoro-imidazo[1,2-a]pyridin-3-ylamino)-N-hydroxy-acetamide | 299.16 | 299.16 |
| 2-(6,8-difluoro-2-isobutyl-imidazo[1,2-a]pyridin-3-ylamino)-N-hydroxy-acetamide | 299.16 | 299.16 |
| 2-(6,8-difluoro-2-pentyl-imidazo[1,2-a]pyridin-3-ylamino)-N-hydroxy-acetamide | 313.18 | 313.18 |
| 2-[6,8-difluoro-2-(2-methylsulfanyl-ethyl)-imidazo[1,2-a]pyridin-3-ylamino]-N-hydroxy-acetamide | 317.11 | 317.12 |
| 2-[2-(2,2-dimethyl-propyl)-6,8-difluoro-imidazo[1,2-a]pyridin-3-ylamino]-N-hydroxy-acetamide | 313.18 | 313.18 |
| 2-(6-bromo-2-isobutyl-7,8-dimethyl-imidazo[1,2-a]pyridin-3-ylamino)-N-hydroxy-acetamide | 369.13 | 369.13 |
| 2-(6-bromo-7,8-dimethyl-2-pentyl-imidazo[1,2-a]pyridin-3-ylamino)-N-hydroxy-acetamide | 383.15 | 383.14 |
| 2-[6-bromo-2-(2,2-dimethyl-propyl)-7,8-dimethyl-imidazo[1,2-a]pyridin-3-ylamino]-N-hydroxy-acetamide | 383.15 | 383.14 |
| 2-(6-bromo-2-hept-1-inyl-7,8-dimethyl-imidazo[1,2-a]pyridin-3-ylamino)-N-hydroxy-acetamide | 407.15 | 407.15 |
| 2-[2-(2,2-dimethyl-propyl)-7-methyl-6-nitro-imidazo[1,2-a]pyridin-3-ylamino]-N-hydroxy-acetamide | 336.20 | 336.21 |
| 2-(5-bromo-2-butyl-imidazo[1,2-a]pyridin-3-ylamino)-N-hydroxy-acetamide | 341.09 | 341.09 |
| 2-(5-bromo-2-ethyl-imidazo[1,2-a]pyridin-3-ylamino)-N-hydroxy-acetamide | 313.05 | 313.06 |
| 2-(5-bromo-2-isobutyl-imidazo[1,2-a]pyridin-3-ylamino)-N-hydroxy-acetamide | 341.09 | 341.10 |
| 2-(5-bromo-2-hydroxymethyl-imidazo[1,2-a]pyridin-3-ylamino)-N-hydroxy-acetamide | 315.02 | 315.04 |
| 2-(2-benzyl-5-bromo-imidazo[1,2-a]pyridin-3-ylamino)-N-hydroxy-acetamide | 375.07 | 374.98 |
| 2-(5-bromo-2-pentyl-imidazo[1,2-a]pyridin-3-ylamino)-N-hydroxy-acetamide | 355.11 | 355.06 |
| 2-(5-bromo-2-methyl-imidazo[1,2-a]pyridin-3-ylamino)-N-hydroxy-acetamide | 299.03 | 299.04 |
| 3-[5-bromo-3-(hydroxycarbamoylmethyl-amino)-imidazo[1,2-a]pyridin-2-yl]-propionic acid | 357.04 | 357.06 |
| 2-(5-bromo-2-propyl-imidazo[1,2-a]pyridin-3-ylamino)-N-hydroxy-acetamide | 327.07 | 327.07 |
| 2-[5-bromo-2-(2-methylsulfanyl-ethyl)-imidazo[1,2-a]pyridin-3-ylamino]-N-hydroxy-acetamide | 359.04 | 359.06 |
| 2-(5-bromo-2-tert-butyl-imidazo[1,2-a]pyridin-3-ylamino)-N-hydroxy-acetamide | 341.09 | 341.17 |
| 2-[5-bromo-2-(2,2-dimethyl-propyl)-imidazo[1,2-a]pyridin-3-ylamino]-N-hydroxy-acetamide | 355.11 | 355.11 |
| 2-(5-bromo-2-hept-1-inyl-imidazo[1,2-a]pyridin-3-ylamino)-N-hydroxy-acetamide | 379.11 | 379.12 |
| 2-(2-butyl-8-ethyl-5-methyl-imidazo[1,2-a]pyridin-3-ylamino)-N-hydroxy-acetamide | 305.24 | 305.23 |
| 2-(8-ethyl-2-hydroxymethyl-5-methyl-imidazo[1,2-a]pyridin-3-ylamino)-N-hydroxy-acetamide | 279.17 | 279.18 |
| 2-(2-benzyl-8-ethyl-5-methyl-imidazo[1,2-a]pyridin-3-ylamino)-N-hydroxy-acetamide | 339.22 | 339.22 |
| 2-(8-ethyl-5-methyl-2-pentyl-imidazo[1,2-a]pyridin-3-ylamino)-N-hydroxy-acetamide | 319.26 | 319.25 |
| 2-[2-(2,2-dimethyl-propyl)-8-ethyl-5-methyl-imidazo[1,2-a]pyridin-3-ylamino]-N-hydroxy-acetamide | 319.26 | 319.25 |
| 2-(8-ethyl-2-hept-1-inyl-5-methyl-imidazo[1,2-a]pyridin-3-ylamino)-N-hydroxy-acetamide | 343.26 | 343.26 |
| 2-(6,8-dichloro-2-hydroxymethyl-imidazo[1,2-a]pyridin-3-ylamino)-N-hydroxy-acetamide | 305.03 | 305.06 |
| 2-(6,8-dichloro-2-pentyl-imidazo[1,2-a]pyridin-3-ylamino)-N-hydroxy-acetamide | 345.12 | 345.12 |
| 2-(6-bromo-2-isobutyl-7-methyl-imidazo[1,2-a]pyridin-3-ylamino)-N-hydroxy-acetamide | 355.11 | 355.11 |
| 2-[6-bromo-2-(2,2-dimethyl-propyl)-7-methyl-imidazo[1,2-a]pyridin-3-ylamino]-N-hydroxy-acetamide | 369.13 | 369.12 |
| 2-(2-butyl-5-ethyl-imidazo[1,2-a]pyridin-3-ylamino)-N-hydroxy-acetamide | 291.22 | 291.22 |
| 2-(5-ethyl-2-isobutyl-imidazo[1,2-a]pyridin-3-ylamino)-N-hydroxy-acetamide | 291.22 | 291.21 |
| 2-(5-ethyl-2-pentyl-imidazo[1,2-a]pyridin-3-ylamino)-N-hydroxy-acetamide | 305.24 | 305.23 |
| 3-[5-ethyl-3-(hydroxycarbamoylmethyl-amino)-imidazo[1,2-a]pyridin-2-yl]-propionic acid | 307.17 | 307.17 |
| 2-(5-ethyl-2-propyl-imidazo[1,2-a]pyridin-3-ylamino)-N-hydroxy-acetamide | 277.20 | 277.19 |

-continued

| Example | calc. [M + H] | found [M + H] |
|---|---|---|
| 2-[5-ethyl-2-(2-methylsulfanyl-ethyl)-imidazo[1,2-a]pyridin-3-ylamino]-N-hydroxy-acetamide | 309.17 | 309.18 |
| 2-(2-tert-butyl-5-ethyl-imidazo[1,2-a]pyridin-3-ylamino)-N-hydroxy-acetamide | 291.22 | 291.22 |
| 2-[2-(2,2-dimethyl-propyl)-5-ethyl-imidazo[1,2-a]pyridin-3-ylamino]-N-hydroxy-acetamide | 305.24 | 305.24 |
| 2-(5-ethyl-2-hept-1-inyl-imidazo[1,2-a]pyridin-3-ylamino)-N-hydroxy-acetamide | 329.24 | 329.24 |
| 2-(6-bromo-2-butyl-5-methyl-imidazo[1,2-a]pyridin-3-ylamino)-N-hydroxy-acetamide | 355.11 | 355.11 |
| 2-(2-benzyl-6-bromo-5-methyl-imidazo[1,2-a]pyridin-3-ylamino)-N-hydroxy-acetamide | 389.09 | 389.06 |
| 2-(6-bromo-5-methyl-2-pentyl-imidazo[1,2-a]pyridin-3-ylamino)-N-hydroxy-acetamide | 369.13 | 369.13 |
| 3-[6-bromo-3-(hydroxycarbamoylmethyl-amino)-5-methyl-imidazo[1,2-a]pyridin-2-yl]-propionic acid | 371.06 | 371.10 |
| 2[6-bromo-5-methyl-2-(2-methylsulfanyl-ethyl)-imidazo[1,2-a]pyridin-3-ylamino]-N-hydroxy-acetamide | 373.06 | 373.08 |
| 2-[6-bromo-2-(2,2-dimethyl-propyl)-5-methyl-imidazo[1,2-a]pyridin-3-ylamino]-N-hydroxy-acetamide | 369.13 | 369.14 |
| 2-(6-bromo-2-hept-1-inyl-5-methyl-imidazo[1,2-a]pyridin-3-ylamino)-N-hydroxy-acetamide | 393.13 | 393.03 |
| 2-(2,7-bis-hydroxymethyl-imidazo[1,2-a]pyridin-3-ylamino)-N-hydroxy-acetamide | 267.13 | 267.13 |
| N-hydroxy-2-(7-hydroxymethyl-2-propyl-imidazo[1,2-a]pyridin-3-ylamino)-acetamide | 279.17 | 279.17 |
| 2-(2-tert-butyl-7-hydroxymethyl-imidazo[1,2-a]pyridin-3-ylamino)-N-hydroxy-acetamide | 293.19 | 293.18 |
| 2-(2-cyclohexyl-7-hydroxymethyl-imidazo[1,2-a]pyridin-3-ylamino)-N-hydroxy-acetamide | 319.21 | 319.20 |
| 2-butyl-3-(hydroxycarbamoylmethyl-amino)-imidazo[1,2-a]pyridine-6-carboxylic acid amide | 306.19 | 306.18 |
| 3-(hydroxycarbamoylmethyl-amino)-2-hydroxymethyl-imidazo[1,2-a]pyridine-6-carboxylic acid amide | 280.12 | 280.14 |
| 2-tert-butyl-3-(hydroxycarbamoylmethyl-amino)-imidazo[1,2-a]pyridine-6-carboxylic acid amide | 306.19 | 306.18 |
| 3-(hydroxycarbamoylmethyl-amino)-2-(3,3,3-trifluoro-propyl)-imidazo[1,2-a]pyridine-6-carboxylic acid amide | 346.13 | 346.15 |
| 2-cyclohexyl-3-(hydroxycarbamoylmethyl-amino)-imidazo[1,2-a]pyridine-6-carboxylic acid amide | 332.21 | 332.20 |
| 2-(6,8-dibromo-2-butyl-5,7-dimethyl-imidazo[1,2-a]pyridin-3-ylamino)-N-hydroxy-acetamide | 447.03 | 447.05 |
| 2-(6,8-dibromo-2-ethyl-5,7-dimethyl-imidazo[1,2-a]pyridin-3-ylamino)-N-hydroxy-acetamide | 419.00 | 419.02 |
| 2-(2-benzyl-6,8-dibromo-5,7-dimethyl-imidazo[1,2-a]pyridin-3-ylamino)-N-hydroxy-acetamide | 481.01 | 481.05 |
| 2-(6,8-dibromo-5,7-dimethyl-2-pentyl-imidazo[1,2-a]pyridin-3-ylamino)-N-hydroxy-acetamide | 461.05 | 461.08 |
| 3-[6,8-dibromo-3-(hydroxycarbamoylmethyl-amino)-5,7-dimethyl-imidazo[1,2-a]pyridin-2-yl]-propionic acid | 462.98 | 463.01 |
| 2-[6,8-dibromo-2-(2,2-dimethyl-propyl)-5,7-dimethyl-imidazo[1,2-a]pyridin-3-ylamino]-N-hydroxy-acetamide | 461.05 | 461.10 |
| 2-[6,8-dibromo-5,7-dimethyl-2-(3,3,3-trifluoro-propyl)-imidazo[1,2-a]pyridin-3-ylamino]-N-hydroxy-acetamide | 486.98 | 487.04 |
| 2-(8-bromo-6-chloro-2-ethyl-imidazo[1,2-a]pyridin-3-ylamino)-N-hydroxy-acetamide | 347.01 | 347.10 |
| 2-[8-bromo-6-chloro-2-(2,2-dimethyl-propyl)-imidazo[1,2-a]pyridin-3-ylamino]-N-hydroxy-acetamide | 389.07 | 389.07 |
| 2-(8-bromo-6-chloro-2-cyclohexyl-imidazo[1,2-a]pyridin-3-ylamino)-N-hydroxy-acetamide | 401.07 | 401.08 |
| 2-(8-amino-2-butyl-6-chloro-imidazo[1,2-a]pyridin-3-ylamino)-N-hydroxy-acetamide | 312.15 | 312.16 |
| 2-(8-amino-6-chloro-2-ethyl-imidazo[1,2-a]pyridin-3-ylamino)-N-hydroxy-acetamide | 284.11 | 284.12 |
| 2-(8-amino-6-chloro-2-hydroxymethyl-imidazo[1,2-a]pyridin-3-ylamino)-N-hydroxy-acetamide | 286.09 | 286.02 |
| 2-(8-amino-2-benzyl-6-chloro-imidazo[1,2-a]pyridin-3-ylamino)-N-hydroxy-acetamide | 346.13 | 346.15 |
| 2-(8-amino-6-chloro-2-pentyl-imidazo[1,2-a]pyridin-3-ylamino)-N-hydroxy-acetamide | 326.17 | 326.18 |
| 3-[8-amino-6-chloro-3-(hydroxycarbamoylmethyl-amino)-imidazo[1,2-a]pyridin-2-yl]-propionic acid | 328.10 | 328.12 |
| 2-(8-amino-6-chloro-2-propyl-imidazo[1,2-a]pyridin-3-ylamino)-N-hydroxy-acetamide | 298.13 | 298.06 |
| 2-(8-amino-2-tert-butyl-6-chloro-imidazo[1,2-a]pyridin-3-ylamino)-N-hydroxy-acetamide | 312.15 | 312.16 |

-continued

| Example | calc. [M + H] | found [M + H] |
|---|---|---|
| 2-[8-amino-6-chloro-2-(2,2-dimethyl-propyl)-imidazo[1,2-a]pyridin-3-ylamino]-N-hydroxy-acetamide | 326.17 | 326.18 |
| 2-[8-amino-6-chloro-2-(3,3,3-trifluoro-propyl)-imidazo[1,2-a]pyridin-3-ylamino]-N-hydroxy-acetamide | 352.10 | 352.05 |
| 2-(8-amino-6-chloro-2-cyclohexyl-imidazo[1,2-a]pyridin-3-ylamino)-N-hydroxy-acetamide | 338.17 | 338.18 |
| 2-(8-amino-6-bromo-2-butyl-imidazo[1,2-a]pyridin-3-ylamino)-N-hydroxy-acetamide | 356.10 | 356.12 |
| 2-(8-amino-6-bromo-2-ethyl-imidazo[1,2-a]pyridin-3-ylamino)-N-hydroxy-acetamide | 328.06 | 328.08 |
| 2-(8-amino-6-bromo-2-hydroxymethyl-imidazo[1,2-a]pyridin-3-ylamino)-N-hydroxy-acetamide | 330.04 | 330.06 |
| 2-(8-amino-2-benzyl-6-bromo-imidazo[1,2-a]pyridin-3-ylamino)-N-hydroxy-acetamide | 390.08 | 390.11 |
| 2-(8-amino-6-bromo-2-pentyl-imidazo[1,2-a]pyridin-3-ylamino)-N-hydroxy-acetamide | 370.12 | 370.13 |
| 2-(8-amino-6-bromo-2-propyl-imidazo[1,2-a]pyridin-3-ylamino)-N-hydroxy-acetamide | 342.08 | 342.10 |
| 2-(8-amino-6-bromo-2-tert-butyl-imidazo[1,2-a]pyridin-3-ylamino)-N-hydroxy-acetamide | 356.10 | 356.11 |
| 2-[8-amino-6-bromo-2-(2,2-dimethyl-propyl)-imidazo[1,2-a]pyridin-3-ylamino]-N-hydroxy-acetamide | 370.12 | 370.13 |
| 2-[8-amino-6-bromo-2-(3,3,3-trifluoro-propyl)-imidazo[1,2-a]pyridin-3-ylamino]-N-hydroxy-acetamide | 396.04 | 396.05 |
| 2-[8-amino-6-bromo-2-(2,2,2-trifluoro-ethyl)-imidazo[1,2-a]pyridin-3-ylamino]-N-hydroxy-acetamide | 382.03 | 382.06 |
| 2-(8-amino-6-bromo-2-cyclohexyl-imidazo[1,2-a]pyridin-3-ylamino)-N-hydroxy-acetamide | 382.12 | 382.13 |
| 2-(6-amino-2-butyl-imidazo[1,2-a]pyridin-3-ylamino)-N-hydroxy-acetamide | 278.19 | 278.19 |
| 2-(6-amino-2-ethyl-imidazo[1,2-a]pyridin-3-ylamino)-N-hydroxy-acetamide | 250.15 | 250.15 |
| 2-(6-amino-2-benzyl-imidazo[1,2-a]pyridin-3-ylamino)-N-hydroxy-acetamide | 312.17 | 312.25 |
| 2-(6-amino-2-pentyl-imidazo[1,2-a]pyridin-3-ylamino)-N-hydroxy-acetamide | 292.21 | 292.20 |
| 3-[6-amino-3-(hydroxycarbamoylmethyl-amino)-imidazo[1,2-a]pyridin-2-yl]-propionic acid | 294.14 | 294.15 |
| 2-(6-amino-2-propyl-imidazo[1,2-a]pyridin-3-ylamino)-N-hydroxy-acetamide | 264.17 | 264.27 |
| 2-(6-amino-2-tert-butyl-imidazo[1,2-a]pyridin-3-ylamino)-N-hydroxy-acetamide | 278.19 | 278.18 |
| 2-[6-amino-2-(2,2-dimethyl-propyl)-imidazo[1,2-a]pyridin-3-ylamino]-N-hydroxy-acetamide | 292.21 | 292.20 |
| 2-[6-amino-2-(3,3,3-trifluoro-propyl)-imidazo[1,2-a]pyridin-3-ylamino]-N-hydroxy-acetamide | 318.14 | 318.15 |
| 2-[6-amino-2-(2,2,2-trifluoro-ethyl)-imidazo[1,2-a]pyridin-3-ylamino]-N-hydroxy-acetamide | 304.12 | 304.11 |
| 2-(6-amino-2-cyclohexyl-imidazo[1,2-a]pyridin-3-ylamino)-N-hydroxy-acetamide | 304.21 | 304.20 |
| 2-(8-amino-2-butyl-imidazo[1,2-a]pyridin-3-ylamino)-N-hydroxy-acetamide | 278.19 | 278.19 |
| 2-(8-amino-2-benzyl-imidazo[1,2-a]pyridin-3-ylamino)-N-hydroxy-acetamide | 312.17 | 312.18 |
| 2-(8-amino-2-pentyl-imidazo[1,2-a]pyridin-3-ylamino)-N-hydroxy-acetamide | 292.21 | 292.20 |
| 2-(8-amino-2-propyl-imidazo[1,2-a]pyridin-3-ylamino)-N-hydroxy-acetamide | 264.17 | 264.20 |
| 2-(8-amino-2-tert-butyl-imidazo[1,2-a]pyridin-3-ylamino)-N-hydroxy-acetamide | 278.19 | 278.19 |
| 2-[8-amino-2-(2,2-dimethyl-propyl)-imidazo[1,2-a]pyridin-3-ylamino]-N-hydroxy-acetamide | 292.21 | 292.20 |
| 2-[8-amino-2-(3,3,3-trifluoro-propyl)-imidazo[1,2-a]pyridin-3-ylamino]-N-hydroxy-acetamide | 318.14 | 318.15 |
| 2-(5-amino-2-butyl-imidazo[1,2-a]pyridin-3-ylamino)-N-hydroxy-acetamide | 278.19 | 278.25 |
| 2-(5-amino-2-benzyl-imidazo[1,2-a]pyridin-3-ylamino)-N-hydroxy-acetamide | 312.17 | 312.19 |
| 2-(5-amino-2-pentyl-imidazo[1,2-a]pyridin-3-ylamino)-N-hydroxy-acetamide | 292.21 | 292.20 |
| 2-(5-amino-2-propyl-imidazo[1,2-a]pyridin-3-ylamino)-N-hydroxy-acetamide | 264.17 | 264.17 |
| 2-(5-amino-2-tert-butyl-imidazo[1,2-a]pyridin-3-ylamino)-N-hydroxy-acetamide | 278.19 | 278.19 |
| 2-[5-amino-2-(3,3,3-trifluoro-propyl)-imidazo[1,2-a]pyridin-3-ylamino]-N-hydroxy-acetamide | 318.14 | 318.16 |

-continued

| Example | calc. [M + H] | found [M + H] |
|---|---|---|
| 2-[5-amino-2-(2,2,2-trifluoro-ethyl)-imidazo[1,2-a]pyridin-3-ylamino]-N-hydroxy-acetamide | 304.12 | 304.10 |
| 2-(5-amino-2-cyclohexyl-imidazo[1,2-a]pyridin-3-ylamino)-N-hydroxy-acetamide | 304.21 | 304.21 |
| 2-(2-butyl-8-methyl-imidazo[1,2-a]pyridin-3-ylamino)-N-hydroxy-acetamide | 277.20 | 277.22 |
| N-hydroxy-2-(2-hydroxymethyl-8-methyl-imidazo[1,2-a]pyridin-3-ylamino)-acetamide | 251.14 | 251.13 |
| 2-(2-benzyl-8-methyl-imidazo[1,2-a]pyridin-3-ylamino)-N-hydroxy-acetamide | 311.18 | 311.11 |
| N-hydroxy-2-(8-methyl-2-pentyl-imidazo[1,2-a]pyridin-3-ylamino)-acetamide | 291.22 | 291.21 |
| 2-[2-(2,2-dimethyl-propyl)-8-methyl-imidazo[1,2-a]pyridin-3-ylamino]-N-hydroxy-acetamide | 291.22 | 291.21 |
| N-hydroxy-2-[8-methyl-2-(3,3,3-trifluoro-propyl)-imidazo[1,2-a]pyridin-3-ylamino]-acetamide | 317.14 | 317.15 |
| 2-(cyclohexyl-8-methyl-imidazo[1,2-a]pyridin-3-ylamino)-N-hydroxy-acetamide | 303.22 | 303.21 |
| 2-(2-butyl-7-ethyl-imidazo[1,2-a]pyridin-3-ylamino)-N-hydroxy-acetamide | 291.22 | 291.21 |
| 2-(7-ethyl-2-hydroxymethyl-imidazo[1,2-a]pyridin-3-ylamino)-N-hydroxy-acetamide | 265.16 | 265.07 |
| 2-(2-benzyl-7-ethyl-imidazo[1,2-a]pyridin-3-ylamino)-N-hydroxy-acetamide | 325.20 | 325.20 |
| 2-(7-ethyl-2-pentyl-imidazo[1,2-a]pyridin-3-ylamino)-N-hydroxy-acetamide | 305.24 | 305.23 |
| 2-(2-cyclohexyl-7-ethyl-imidazo[1,2-a]pyridin-3-ylamino)-N-hydroxy-acetamide | 317.24 | 317.23 |
| 2-(2-butyl-8-hydroxy-imidazo[1,2-a]pyridin-3-ylamino)-N-hydroxy-acetamide | 279.17 | 279.20 |
| 2-(2-ethyl-8-hydroxy-imidazo[1,2-a]pyridin-3-ylamino)-N-hydroxy-acetamide | 251.14 | 251.14 |
| N-hydroxy-2-(8-hydroxy-2-hydroxymethyl-imidazo[1,2-a]pyridin-3-ylamino)-acetamide | 253.11 | 253.12 |
| 2-(2-benzyl-8-hydroxy-imidazo[1,2-a]pyridin-3-ylamino)-N-hydroxy-acetamide | 313.15 | 313.17 |
| N-hydroxy-2-(8-hydroxy-2-pentyl-imidazo[1,2-a]pyridin-3-ylamino)-acetamide | 293.19 | 293.19 |
| N-hydroxy-2-(8-hydroxy-2-propyl-imidazo[1,2-a]pyridin-3-ylamino)-acetamide | 265.16 | 265.16 |
| 2-(2-tert-butyl-8-hydroxy-imidazo[1,2-a]pyridin-3-ylamino)-N-hydroxy-acetamide | 279.17 | 279.17 |
| 2-[2-(2,2-dimethyl-propyl)-8-hydroxy-imidazo[1,2-a]pyridin-3-ylamino]-N-hydroxy-acetamide | 293.19 | 293.19 |
| N-hydroxy-2-[8-hydroxy-2-(3,3,3-trifluoro-propyl)-imidazo[1,2-a]pyridin-3-ylamino]-acetamide | 319.12 | 319.13 |
| 2-(2-cyclohexyl-8-hydroxy-imidazo[1,2-a]pyridin-3-ylamino)-N-hydroxy-acetamide | 305.19 | 305.19 |
| 2-(2-butyl-imidazo[2,1-a]isoquinolin-3-ylamino)-N-hydroxy-acetamide | 313.20 | 313.20 |
| 2-(2-benzyl-imidazo[2,1-a]isoquinolin-3-ylamino)-N-hydroxy-acetamide | 347.18 | 347.19 |
| N-hydroxy-2-(2-pentyl-imidazo[2,1-a]isoquinolin-3-ylamino)-acetamide | 327.22 | 327.22 |
| 2-[2-(2,2-dimethyl-propyl)-imidazo[2,1-a]isoquinolin-3-ylamino]-N-hydroxy-acetamide | 327.22 | 327.22 |
| 2-(2-cyclohexyl-imidazo[2,1-a]isoquinolin-3-ylamino)-N-hydroxy-acetamide | 339.22 | 339.21 |
| 2-(8-benzyloxy-2-butyl-imidazo[1,2-a]pyridin-3-ylamino)-N-hydroxy-acetamide | 369.23 | 369.23 |
| 2-(8-benzyloxy-2-hydroxymethyl-imidazo[1,2-a]pyridin-3-ylamino)-N-hydroxy-acetamide | 343.17 | 343.18 |
| 2-(8-benzyloxy-2-pentyl-imidazo[1,2-a]pyridin-3-ylamino)-N-hydroxy-acetamide | 383.25 | 383.23 |
| 2-(8-benzyloxy-2-propyl-imidazo[1,2-a]pyridin-3-ylamino)-N-hydroxy-acetamide | 355.21 | 355.22 |
| 2-(8-benzyloxy-2-tert-butyl-imidazo[1,2-a]pyridin-3-ylamino)-N-hydroxy-acetamide | 369.23 | 369.25 |
| 2-[8-benzyloxy-2-(2,2-dimethyl-propyl)-imidazo[1,2-a]pyridin-3-ylamino]-N-hydroxy-acetamide | 383.25 | 383.25 |
| 2-(8-benzyloxy-2-cyclohexyl-imidazo[1,2-a]pyridin-3-ylamino)-N-hydroxy-acetamide | 395.25 | 395.25 |
| 3-(hydroxycarbamoylmethyl-amino)-2-pentyl-imidazo[1,2-a]pyridine-6-carboxylic acid | 321.19 | 321.14 |
| 2-butyl-3-(hydroxycarbamoylmethyl-amino)-imidazo[1,2-a]pyridine-8-carboxylic acid | 307.17 | 307.20 |

-continued

| Example | calc. [M + H] | found [M + H] |
|---|---|---|
| 3-(hydroxycarbamoylmethyl-amino)-2-pentyl-imidazo[1,2-a]pyridine-8-carboxylic acid | 321.19 | 321.17 |
| 2-(2,2-dimethyl-propyl)-3-(hydroxycarbamoylmethyl-amino)-imidazo[1,2-a]pyridine-8-carboxylic acid | 321.19 | 321.19 |
| 2-cyclohexyl-3-(hydroxycarbamoylmethyl-amino)-imidazo[1,2-a]pyridine-8-carboxylic acid | 333.19 | 333.20 |

I claim:

1. Compounds of formula (I)

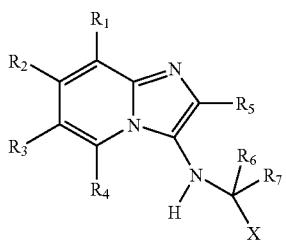

wherein the radicals $R^1$, $R^2$, $R^3$ and $R^4$, independently of one another, are a hydrogen atom, a halogen atom, a hydroxy, amino, nitro or thiole group, an alkyl, alkenyl, alkinyl, heteroalkyl, aryl, heteroaryl, cycloalkyl, alkylcycloalkyl, heteroalkylcycloalkyl, heterocycloalkyl, aralkyl or a heteroaralkyl radical, whereby all of these radicals may optionally be substituted, or two of the radicals $R^1$, $R^2$, $R^3$ and $R^4$ together may be part of a cycloalkyl, heterocycloalkyl, aryl or heteroaryl ring, whereby each of these rings may optionally be substituted;

$R^5$ is a hydrogen atom, a halogen atom, a hydroxy, amino, nitro or thiole group, an alkyl, alkenyl, alkinyl, heteroalkyl, aryl, heteroaryl, cycloalkyl, alkylcycloalkyl, heteroalkylcycloalkyl, heterocycloalkyl, aralkyl or heteroaralkyl radical;

the radicals $R^6$ and $R^7$, independently of one another, are a hydrogen atom, or an alkyl, alkenyl, alkinyl, heteroalkyl, aryl, heteroaryl, cycloalkyl, alkylcycloalkyl, heteroalkylcycloalkyl, heterocycloalkyl, aralkyl or heteroaralkyl radical, whereby all these radicals may optionally be substituted; and X is a group of formula —CO—NHOH, —NOH—CHO, —CH$_2$—NOH—CHO, or is selected from the following formulae:

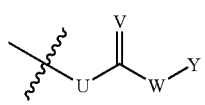

whereby U is a bond, CH$_2$, NH, O or S, V is O, S, NH or CH$_2$, W is O, S, NH or CH$_2$, and Y is OH or NH$_2$, or a pharmaceutically acceptable salt, or a pharmaceutically acceptable formulation thereof.

2. Compounds according to claim 1, whereby $R^1$ is a hydrogen atom, a chlorine atom, a bromine atom, an amino group, a methyl group or an ethyl group.

3. Compounds according to claim 1, whereby $R^2$ is a hydrogen atom, a chlorine atom, a bromine atom, a methyl group or an ethyl group.

4. Compounds according to claim 1, whereby $R^3$ and $R^4$ are not hydrogen atoms at the same time.

5. Compounds according to claim 1, whereby $R^3$ is a hydrogen atom, a chlorine atom, a bromine atom, an amino group, a methyl group, an ethyl group or a propyl group.

6. Compounds according to claim 1, whereinby $R^4$ is a chlorine atom, a bromine atom, a methyl group, an ethyl group or a propyl group.

7. Compounds according to claim 1, in which $R^3$ is a bromine atom and $R^4$ is a methyl group, or in which $R^3$ is a hydrogen atom and $R^4$ is a chlorine atom or a bromine atom.

8. Compounds according to claim 1, in which $R^5$ is a tert-butyl group, an isopropyl group, a neopentyl group or a n-hexyl group.

9. Compounds according to claim 1, in which the groups $R^6$ and $R^7$, independently of one another, are hydrogen atoms, hydroxymethyl groups or methyl groups.

10. Compounds according to claim 1, whereby X is a group of formula CO—NH—OH.

11. Pharmaceutical composition which contains a compound according to claim 1 and optionally carriers and/or adjuvants.

12. Compounds of formula (I)

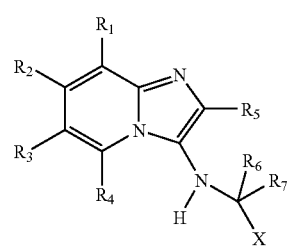

wherein the radicals $R^1$, $R^2$, and $R^3$, independently of one another, are a hydrogen atom, a halogen atom, a hydroxy, amino, nitro or thiole group, an alkyl, alkenyl, alkinyl, heteroalkyl, aryl, heteroaryl, cycloalkyl, alkylcycloalkyl, heteroalkylcycloalkyl, heterocycloalkyl, aralkyl or a heteroaralkyl radical, whereby all of these radicals may optionally be substituted, or two of the radicals $R^1$, $R^2$, and $R^3$ together may be part of a cycloalkyl, heterocycloalkyl, aryl or heteroaryl ring, whereby each of these rings may optionally be substituted;

$R^4$ is a chlorine atom, a bromine atom, a methyl group, an ethyl group or a propyl group;

$R^5$ is a hydrogen atom, a halogen atom, a hydroxy, amino, nitro or thiole group, an alkyl, alkenyl, alkinyl, heteroalkyl, aryl, heteroaryl, cycloalkyl, alkylcycloalkyl, heteroalkylcycloalkyl, heterocycloalkyl, aralkyl or heteroaralkyl radical;

the radicals $R^6$ and $R^7$, independently of one another, are a hydrogen atom, or an alkyl, alkenyl, alkinyl, heteroalkyl, aryl, heteroaryl, cycloalkyl, alkylcycloalkyl, heteroalkylcycloalkyl, heterocycloalkyl, aralkyl or heteroaralkyl radical, whereby all these radicals may optionally be substituted; and X is a group of formula —CS—NHOH, —CH$_2$—CO—CH$_2$—OH, —CO—CH$_2$—OH, —CO—NHOH, —CNH—NHOH, —CH$_2$—NOH—CHS, —NOH—CHS, —NOH—CHO, —CH$_2$—NOH—CHO, —CH$_2$—CHOH—CHO, —CHOH—CHO, —CHOH—COOH, —CH(CH$_2$—OH)—COOH, —COOH or —CH$_2$COOH, or is selected from the following formulae:

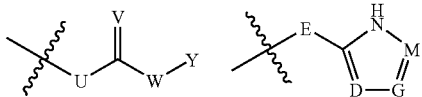

whereby U is a bond, CH$_2$, NH, O or S, V is O, S, NH or CH$_2$, W is O, S, NH or CH$_2$, and Y is OH or NH$_2$, E is a bond, CH$_2$, NH, O or S and the groups D, G and M, independently of one another, are N or CH, or a pharmaceutically acceptable salt or a pharmaceutically acceptable formulation thereof.

13. Compounds according to claim 12, whereby $R^1$ is a hydrogen atom, a chlorine atom, a bromine atom, an amino group, a methyl group or an ethyl group.

14. Compounds according to claim 12, whereby $R^2$ is a hydrogen atom, a chlorine atom, a bromine atom, a methyl group or an ethyl group.

15. Compounds according to claim 12, whereby $R^3$ and $R^4$ are not hydrogen atoms at the same time.

16. Compounds according to claim 12, whereby $R^3$ is a hydrogen atom, a chlorine atom, a bromine atom, an amino group, a methyl group, an ethyl group or a propyl group.

17. Compounds according to claim 12, in which $R^3$ is a bromine atom and $R^4$ is a methyl group, or in which $R^3$ is a hydrogen atom and $R^4$ is a chlorine atom or a bromine atom.

18. Compounds according to claim 12, in which $R^5$ is a tert-butyl group, an isopropyl group, a neopentyl group or a n-hexyl group.

19. Compounds according to claim 12, in which the groups $R^6$ and $R^7$, independently of one another, are hydrogen atoms, hydroxymethyl groups or methyl groups.

20. Compounds according to claim 12, whereby X is a group of formula —CO—NH—OH.

* * * * *